United States Patent [19]

Schendel

[11] Patent Number: 5,883,230
[45] Date of Patent: Mar. 16, 1999

[54] MULTIDOMAIN HEMATOPOIESIS STIMULATORS

[75] Inventor: Paul Schendel, Wayland, Mass.

[73] Assignee: Genetics Institute, Inc., Cambridge, Mass.

[21] Appl. No.: 658,762

[22] Filed: Jun. 5, 1996

Related U.S. Application Data

[63] Continuation of Ser. No. 57,198, May 5, 1993, abandoned, which is a continuation of Ser. No. 575,003, Aug. 29, 1990, abandoned.

[51] Int. Cl.[6] .................................................. C07K 14/52
[52] U.S. Cl. ............................ 530/351; 530/399; 514/12
[58] Field of Search .......................... 435/69.51, 69.52, 435/69.5, 320.1, 69.7, 240.1, 240.2, 172.3, 252.3; 536/23.5, 23.4; 530/350, 399, 351; 514/2, 12

[56] References Cited

U.S. PATENT DOCUMENTS

| | | |
|---|---|---|
| 4,675,382 | 6/1987 | Murphy . |
| 4,691,009 | 9/1987 | Palmer . |
| 4,935,233 | 6/1990 | Bell et al. . |
| 5,032,395 | 7/1991 | Clark et al. . |
| 5,071,761 | 12/1991 | Meyer et al. . |
| 5,073,627 | 12/1991 | Curtis et al. . |
| 5,095,096 | 3/1992 | Mike et al. . |
| 5,108,910 | 4/1992 | Curtis et al. . |
| 5,166,322 | 11/1992 | Shaw et al. . |
| 5,215,895 | 6/1993 | Bennett et al. . |
| 5,567,611 | 10/1996 | Ralph et al. . |

FOREIGN PATENT DOCUMENTS

| | | |
|---|---|---|
| WO 88/00971 | 2/1988 | WIPO . |
| WO 90/1287 | 11/1990 | WIPO . |
| WO 91/01004 | 1/1991 | WIPO . |
| WO 91/02754 | 3/1991 | WIPO . |
| WO 92/06116 | 4/1992 | WIPO . |

OTHER PUBLICATIONS

Chase, "Immunex Refines Gene–Splicing Method to Enable Making of Biological 'Cocktail'", *Wall Street Journal*, Sec. B2 (Aug. 29, 1990).
Emerson et al., J. Clin. Invest. 82:1282 (1988).
Kishimoto et al., CA. 112:97051j (1990).
Sino et al., Febs 199(2);187 (1986).
Bulow, L., *Biochem. Soc. Symp.*, 57:123–33, 1990.
Phelps, J.L. et al., *J. Immunol.*, 145(4) :1200–4, 1990.

*Primary Examiner*—Patricia A. Duffy
*Attorney, Agent, or Firm*—Steven R. Lazar

[57] ABSTRACT

A novel fusion protein, IL3-X or X-IL3 wherein X is a hematopoietin fused to IL3.

1 Claim, 5 Drawing Sheets

MULTIDOMAIN HEMATOPOIESIS STIMULATORS

This application is a continuation of application Ser. No. 08/057,198, filed May 5, 1993 now abandoned, which is a file wrapper continuation of application Ser. No. 07/575,003, filed Aug. 29, 1990 now abandoned.

The present invention relates to molecules characterized by more than one active lymphokine domain. More specifically, the invention relates to fusion molecules characterized by the presence of interleukin 3 [IL-3] fused to at least a second lymphokine, the fusion molecule characterized by enhanced IL-3 activity or enhanced activity of both lymphokine fusion molecules.

BACKGROUND OF THE INVENTION

Hematopoietins, or hematopoietic growth factors are regulatory proteins that deliver signals between cells of the immune system, and thereby promote the survival, growth and differentiation of hematopoietic cells. These regulatory molecules include all of the colony-stimulating factors (GM-CSF, G-CSF, M-CSF, and multi CSF or interleukin-3), the interleukins (IL-1 through IL-11), the interferons (alpha, beta and gamma), the tumor necrosis factors (alpha and beta) and leukemia inhibitory factor (LIF). These molecules exhibit a wide range of biologic activities with target cells from bone marrow, peripheral blood, fetal liver, and other lymphoid or hematopoietic organs. See, e.g., G. Wong and S. Clark, *Immunology Today*, 9(5):137 (1988).

The biochemical and biological identification and characterization of certain of these regulatory molecules of the immune system was hampered by the small quantities of the naturally occurring factors available from natural sources, e.g., blood and urine. Many of the hematopoietic molecules have recently been molecularly cloned, heterologously expressed and purified to homogeneity. [D. Metcalf, "The Molecular Biology and Functions of the Granulocyte-Macrophage Colony Stimulating Factors," *Blood*, 67(2):257–267 (1986).] Among these molecules are gamma interferon, human and murine GM-CSF, human G-CSF, human CSF-1 and human and murine IL-3. Several of these purified factors have been found to demonstrate regulatory effects on the hematopoietic and immune systems in vivo, including GM-CSF, G-CSF, IL-3 and IL-2.

There remains a need in the art for additional molecules of therapeutic use which are capable of stimulating or enhancing immune responsiveness for treatment of the wide variety of immune disorders, including e.g., radiation exposure, AIDS, and other disorders characterized by malfunction or disfunction of the immune system.

BRIEF SUMMARY OF THE INVENTION

In one aspect the present invention provides a novel fusion protein of the formula IL3-X or X-IL3, wherein X represents another molecule normally useful in stimulating or enhancing the function of the immune system. X may include, without limitation, natural or modified forms of such molecules as IL-1 through IL-11, G-CSF, GM-CSF and erythropoietin. Presently preferred molecules are those wherein X is IL-3, IL-7, IL-9, IL-11, GM-CSF or G-CSF. This fusion molecule of the present invention is also characterized by being substantially free from other mammalian proteins. The fusion molecule may be characterized by having the usual activity of both of the peptides forming the fusion molecule or it may be further characterized by having a biological or physiological activity greater than simply the additive function of the presence of IL3 or X. The fusion molecule may also unexpectedly provide an enhanced effect on the activity of each of the fusion protein or an activity different from that expected by the presence of IL3 or X.

Another aspect of the invention includes DNA sequences which encode an IL3-X or X-IL3 fusion molecule. These fusion molecule sequences are characterized by DNA sequences encoding IL-3 and X, as well as optional DNA sequences comprising linkers to bring the fusion molecules within a preferred proximity to each other.

Also provided by the present invention is a vector containing a DNA sequence encoding the fusion molecule IL3-X or X-IL3 in operative association with necessary regulatory sequences to control expression of the fusion sequence in appropriate host cells. Host cells transformed with such vectors for use in producing recombinant IL3-X or X-IL3 are also provided by the present invention.

Another aspect of this invention provides pharmaceutical compositions containing a therapeutically effective amount of a fusion molecule IL3-X or X-IL3. These pharmaceutical compositions may be employed in methods for treating cancer, and other disease states responsive to the enhanced presence of IL-3 and its fusion partner, X. Thus, generally this fusion protein may be employed in the treatment of diseases characterized by a deficiency in the number or level of activity of hematopoietic cells.

A further aspect of the invention, therefore, is a method for treating cancer and/or other pathological states which may benefit from enhanced hematopoietic cell functions by administering to a patient a therapeutically effective amount of the fusion protein IL3-X or X-IL3 in a suitable pharmaceutical carrier. These therapeutic methods may include administering simultaneously or sequentially with the fusion molecule an effective amount of at least one other cytokine, hematopoietin, interleukin, growth factor, or antibody.

Still a further aspect of the present invention is a process for producing the fusion protein IL3-X or X-IL3, employing the vectors and transformed cells of the invention. In this process a selected host cell transformed with a DNA sequence encoding an IL3-X or X-IL3 protein in operative association with an expression control sequence is cultured under conditions suitable for growth of the host cell. This claimed process may employ a number of known cells as host cells for expression of the fusion protein. Presently preferred cell lines are mammalian cell lines, fungal cells and bacterial cells.

Other aspects and advantages of the present invention will be apparent upon consideration of the following detailed description of preferred embodiments thereof.

BRIEF DESCRIPTION OF THE DRAWINGS

FIG. I is a schematic diagram of vector construction for use in the expression of an IL3-IL3 fusion molecule.

FIG. II is a schematic diagram of vector construction for use in the expression of an IL3-GMCSF fusion molecule.

Figure 1:
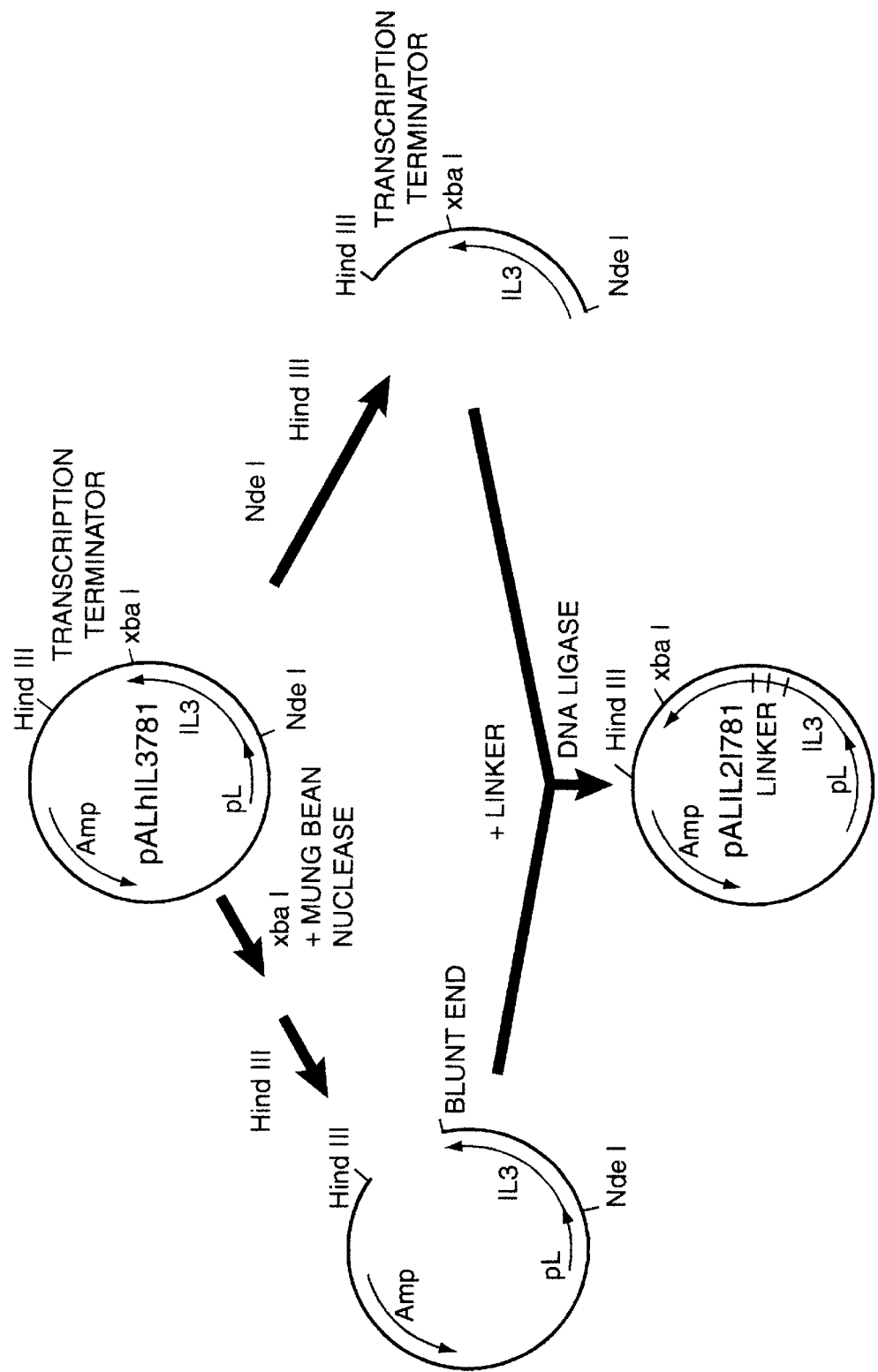
Figure 2:
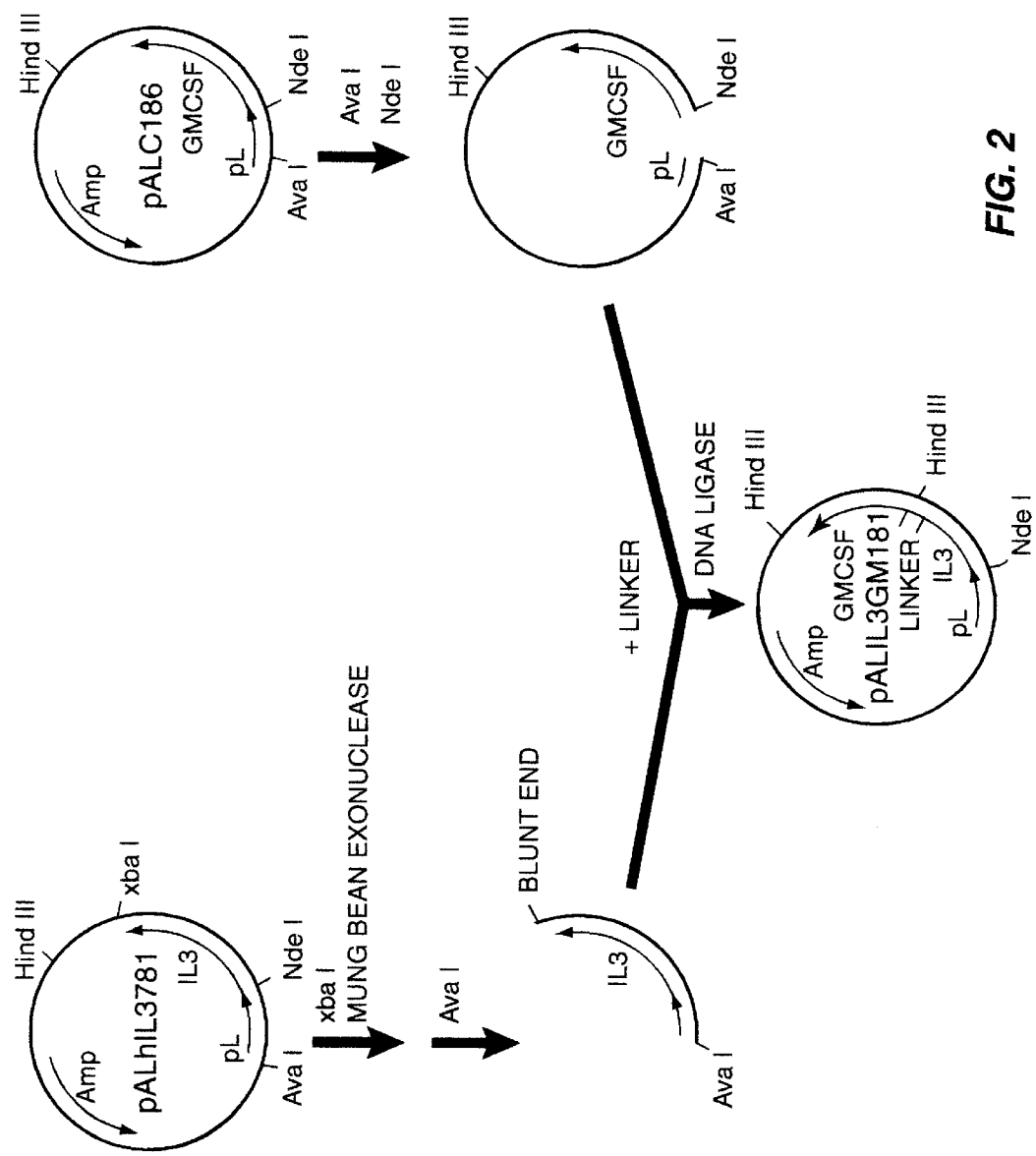
Figure 3:
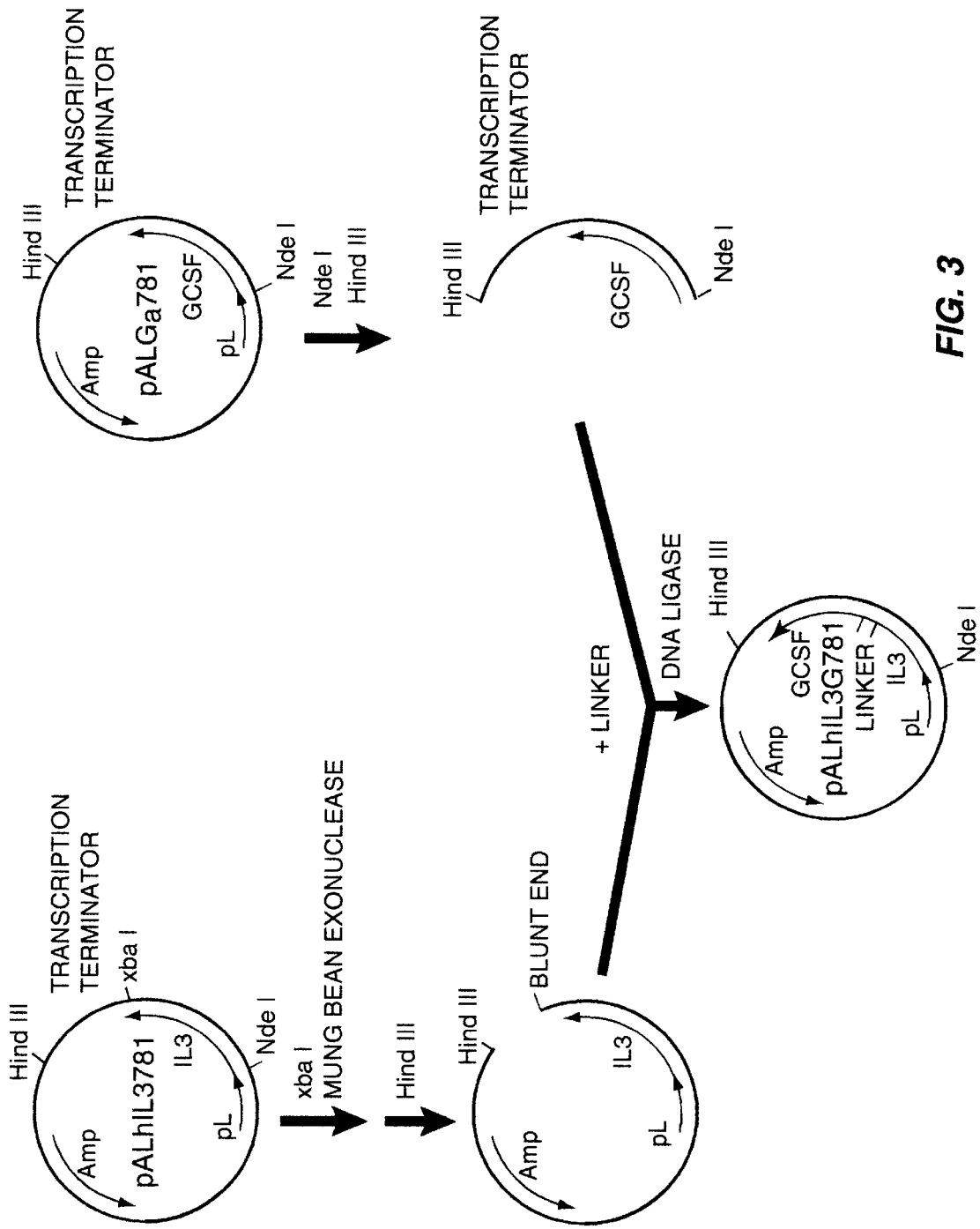
Figure 4:
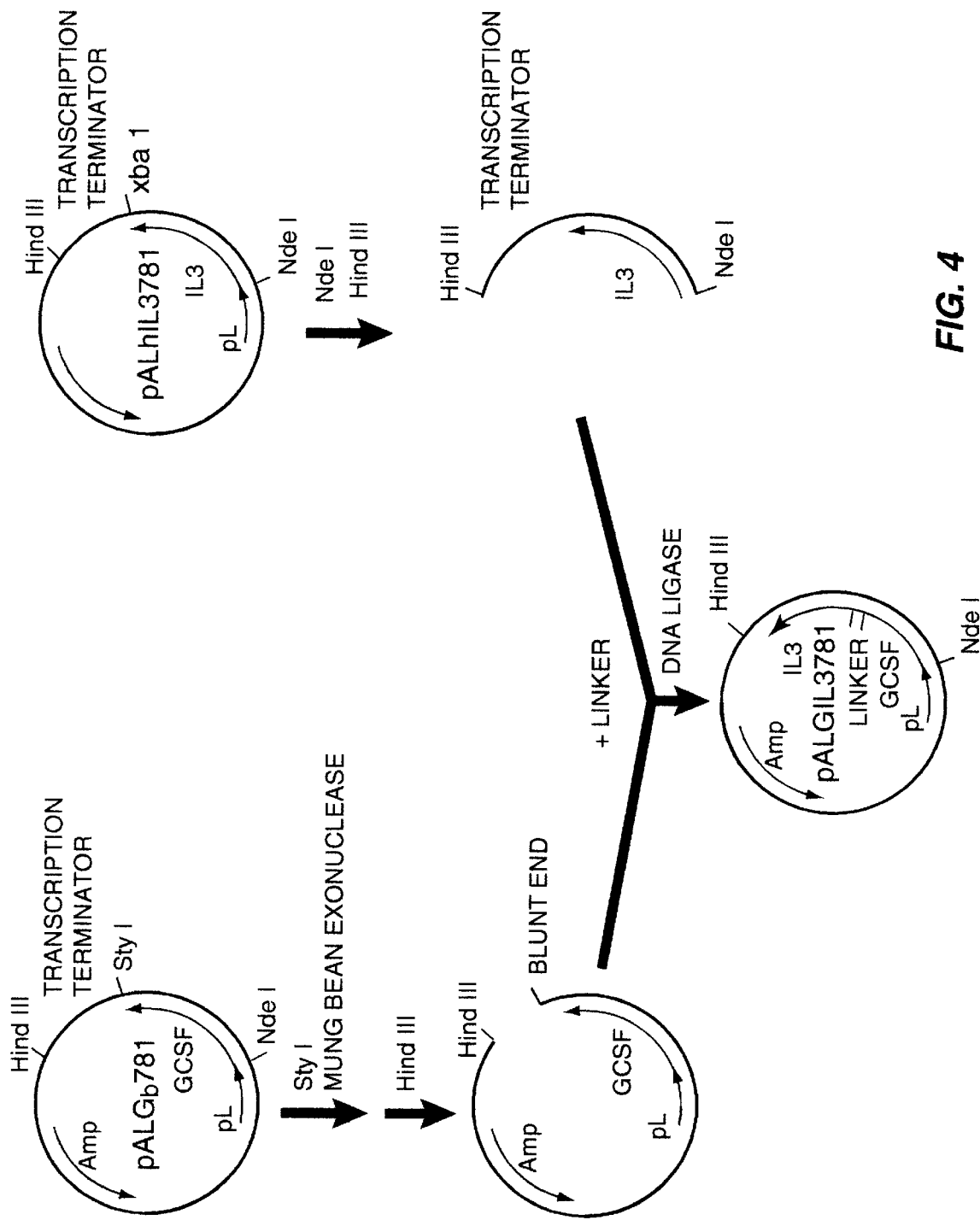
Figure 5:
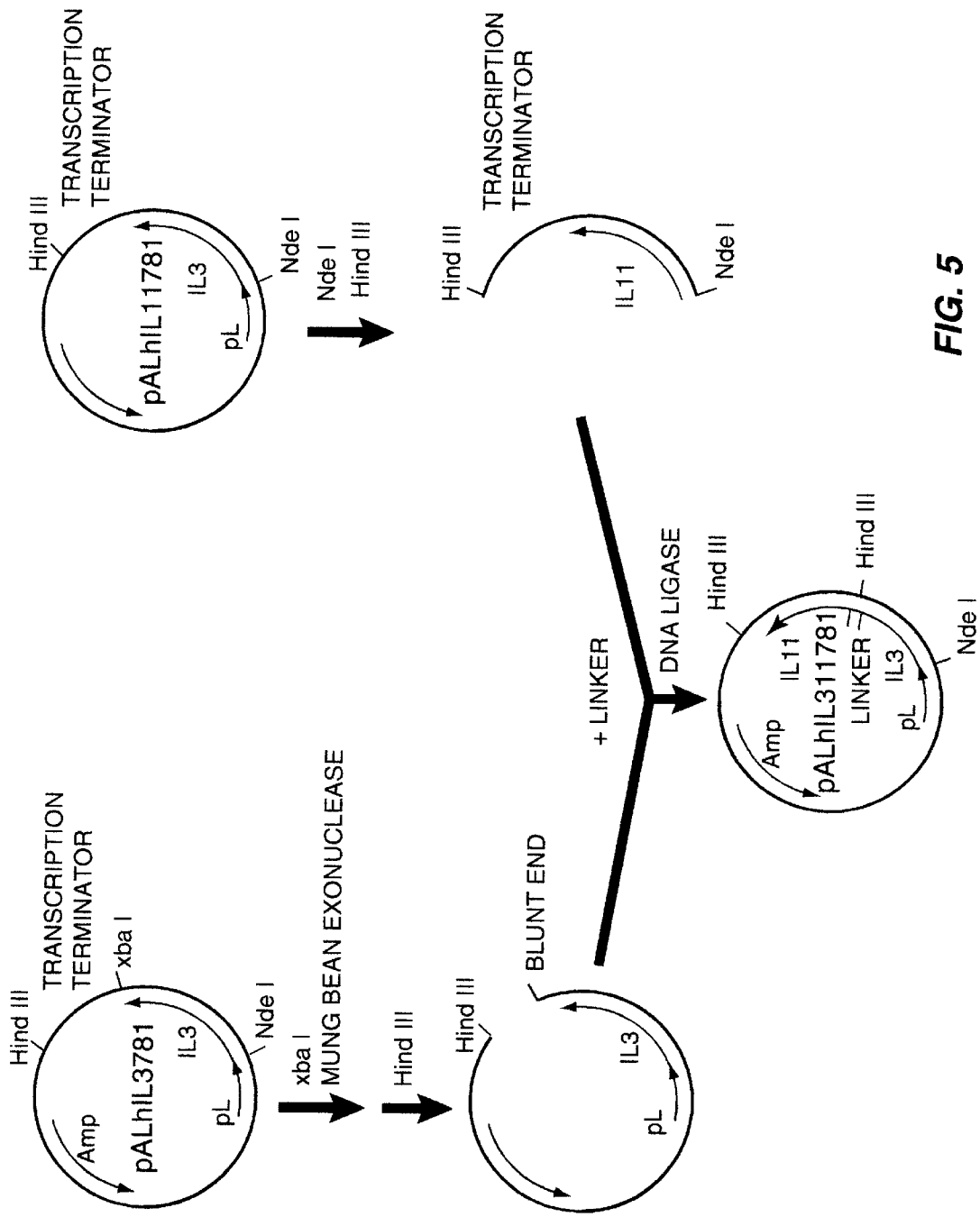

FIG. III is a schematic diagram of vector construction for use in the expression of an IL3-GCSF fusion molecule.

FIG. IV is a schematic diagram of vector construction for use in the expression of a GCSF-IL3 fusion molecule.

FIG. V is a schematic diagram of vector construction for use in the expression of an IL3-IL11 fusion molecule.

DETAILED DESCRIPTION OF THE INVENTION

The novel IL3-X or X-IL3 fusion protein provided by the present invention is a homogeneous protein or proteinaceous composition substantially free of association with other mammalian proteinaceous materials. The entity X in the above formulae represents a lymphokine, the DNA coding sequence of which is fused in frame with the DNA coding region of IL3 either directly or through a linker. By "fused in frame" is meant that there is no translational terminator between the reading frames of the IL3 and X proteins. As used herein, the term "directly" defines fusion of the DNA sequences encoding X and IL-3 without a peptide linker. The X entity may be fused to either the 5' or 3' end of the IL3 molecule.

The DNA and protein sequences of the IL3 molecule are published and may be constructed by a variety of techniques now standard in the art. See, e.g., PCT/US87/01702, incorporated herein by reference.

The proteins encompassed by the present invention are not limited by the particular identity of X, nor to the number of X entities employed in one multi-domain molecule. A non-exclusive list of lymphokines which can comprise the definition of X includes GM-CSF, G-CSF, erythropoietin, IL1, IL2, IL3, IL4, IL6 IL-7, IL-9, IL-11 or B cell stimulatory factor. Presently preferred X molecules include IL-11, IL-3, GM-CSF and GCSF. However, other multidomain molecules employing other X molecules may also prove desirable. Additionally, this invention encompasses the use of modified X molecules or mutated or modified DNA sequences encoding these X molecules. Polypeptide and DNA sequences for these lymphokines are published in the art, as are methods for obtaining expression thereof through recombinant or chemical synthetic techniques. U.S. patent application Ser. No. 07/526,474 is incorporated by reference herein to provide disclosure relating to obtaining the sequence for IL-11.

Fusing of the IL3 sequence to the sequence of X may be accomplished by use of intermediate vectors as described in the examples below. Alternatively, the IL3 sequence can be inserted directly into a vector which contains the X protein coding region, or vice versa. Techniques for cloning DNA sequences in phages or plasmids are known to those of skill in the art. Thus, the gene for the fusion protein IL3-GCSF, for example, is constructed in a vector comprising DNA sequences encoding the two domains fused in frame with one another and operatively linked either directly or through a peptide linker to a regulatory region capable of controlling The fusion may be performed by conventional techniques. [See e.g., Sambrook et al, "Molecular Cloning. A Laboratory Manual", Cold Spring Harbor Laboratory (1989)].

Linkers and adapters can be used for joining the IL3 and X sequences, as well as replacing lost sequences, where a restriction site employed was internal to the region of interest. The linkers joining the two molecules are preferably designed to allow the IL-3 and X proteins to fold and act independently of one another. The sequence of one exemplary linker used in the present examples was based on a sequence found in the HIV-1 reverse transcriptase, and is thought to bridge the C-terminal domain of that protein to the penultimate domain. This peptide is known to be susceptible to mild proteolysis and thus is thought to be on the outside surface of the protein. The sequence is highly charged which should increase the solubility of any protein containing it. In fusing the IL3 and X molecules, multiple copies of the linker sequence of choice may be inserted between the two molecules. The present invention is, however, not limited by the form, size or number of linker sequences employed. The only requirement for the linker sequence is that it functionally does not interfere adversely with the folding of the individual components of the fusion molecule. Moreover, such linkers may be completely absent in a directly fused IL3-X or X-IL3 molecule.

Vectors for use in the construction of the fusion molecules and in the method of expression of the novel IL3-X or X-IL3 fusion proteins also form part of this invention. Vectors containing the IL3-X or X-IL3 DNA sequences which code for fusion proteins of the invention or vectors incorporating modified sequences as described herein are also embodiments of the present invention and useful in the production of IL3-X or X-IL3 proteins.

The vectors employed in the method also contain selected regulatory sequences in operative association with the DNA coding sequences of the invention and capable of directing the replication and expression thereof in selected host cells. The use of regulatory regions for controlling transcription of the fusion genes may allow for growing the host cells to high density with no or low levels of expression of the fusion gene, and then inducing expression by changing the environmental conditions, such as nutrient, temperature, and the like.

The present invention also encompasses the novel fusion DNA sequences, free of association with DNA sequences encoding other primate proteins, and encoding IL3-X or X-IL3 fusion proteins. Variations of DNA sequences encoding the IL3 and X peptide sequences are also included in the fusion molecule of the present invention as well as analogs or derivatives thereof. DNA sequences which code for IL3 and X polypeptides but which differ in codon sequence from naturally occurring IL3 or X, due to the degeneracies of the genetic code or allelic variations (naturally-occurring base changes in the species population which may or may not result in an amino acid change) are also encompassed by this invention. Variations in the DNA sequence of IL3 or X which are caused by point mutations or by induced modifications to enhance the activity, half-life or production of the fusion protein encoded thereby are also encompassed in the invention.

Modifications in the peptides or DNA sequences forming the fusion molecules of the present invention can be made by one skilled in the art using known techniques. Modifications of interest in the IL3 or X sequences may include the replacement, insertion or deletion of a selected amino acid residue in the coding sequences thereof, the insertion or destruction of a glycosylation site or other known peptide modifications. Such modifications may be made in the components of the fusion molecules to enhance the biological properties thereof. Mutagenic techniques for such replacement, insertion or deletion are well known to one skilled in the art. [See, e.g., United States patent 4,518,584.]

Other analogs and derivatives of the sequences of IL3 or X which would be expected to retain that molecules biological or physiological activity in whole or in part may also be easily made by one of skill in the art for use in the fusion molecule of the present invention given the disclosures herein. One such modification may be the attachment of polyethylene glycol onto existing lysine residues in IL3, X or in the linker peptide region. Such modifications are believed to be encompassed by this invention.

The present invention also provides a method for producing IL3-X or X-IL3 fusion molecules. The method of the present invention involves culturing a suitable cell or cell line, which has been transformed with a DNA sequence coding on expression for an IL3-X or X-IL3 fusion molecule under the control of known regulatory sequences. Suitable cells are bacterial cells. For example, the various strains of E. coli (e.g., HB101, MC1061 and strains used in the following examples) are well-known as host cells in the field of biotechnology. Various strains of *B. subtilis*, Pseudomonas, other bacilli and the like may also be employed in this method.

Possibly useful as host cells or cell lines suitable for the present invention are mammalian cells. The selection of suitable cells and methods for transformation, culture, amplification, screening and product production and purification are known in the art. See, e.g., Gething and Sambrook, *Nature*, 293:620–625 (1981); Kaufman et al, *Mol. Cell. Biol.*, 5(7):1750–1759 (1985) or Howley et al, U.S. Pat. No. 4,419,446.

Yeast cells, fungal cells, or insect cells known to those skilled in the art may also be useful as host cells for expression of the fusion molecules of the present invention. See, e.g. Miller et al, *Genetic Engineering*, 8:277–298 (Plenum Press 1986) and references cited therein.

The isolation of the fusion protein of the invention from a cell lysate or extract of the culture medium in any of the above described host cells may be performed by conventional protein isolation techniques.

Thus IL3-X or X-IL3 produced recombinantly, may be used in the treatment of a number of pathological or disease states, particularly those characterized by a decreased level of either myeloid, erythroid, lymphoid, or megakaryocyte cells of the hematopoietic system or combinations thereof. In addition they may be used to activate mature myeloid and/or lymphoid cells. For example the IL3-IL11 fusion molecule may be useful in stimulating the production and/or development of mega-karyocytes and platelets. Among conditions susceptible to treatment with the polypeptides of the present invention is leukopenia, a reduction in the number of circulating leukocytes (white cells) in the peripheral blood. Leukopenia may be induced by exposure to certain viruses or to radiation. It is often a side effect of various forms of cancer therapy, e.g., exposure to chemotherapeutic drugs. Therapeutic treatment of leukopenia with these IL3-X or X-IL3 fusion protein compositions may avoid undesirable side effects caused by treatment with presently available drugs. Additionally the multi-domain facet of the proteins of this invention may allow lower dosages of the fusion protein compositions to be administered in comparison to administration of the individual IL3 or X lymphokines alone.

Various immunodeficiencies or immune disorders may also be beneficially effected by treatment with the polypeptides of the present invention. These factors, alone or in combination with other treatment regimens may be useful in treating or correcting immunodeficiencies which are the result of viral infections, e.g., HIV, HTLVI or HTLVII, severe exposure to radiation, cancer therapy or the result of other medical treatment. Depending on the identification of X, the fusion protein of the present invention may be used to treat other blood cell deficiencies, including thrombocytopenia (platelet deficiency), or anemia (red cell deficiency). Other uses for these novel polypeptides are in the treatment of patients recovering from bone marrow transplants.

Therefore, as yet another aspect of the invention are methods and therapeutic compositions for treating the conditions referred to above. Such compositions comprise a therapeutically effective amount of the fusion protein IL3-X or X-IL3 of the present invention in admixture with a pharmaceutically acceptable carrier. This composition can be systematically administered parenterally. Alternatively, the composition may be administered intravenously. If desirable, the composition may be administered subcutaneously. When systematically administered, the therapeutic composition for use in this invention is in the form of a pyrogen-free, parenterally acceptable aqueous solution. The preparation of such a pharmaceutically acceptable protein solution, having due regard to pH, isotonicity, stability and the like, is within the skill of the art.

The therapeutic method and compositions of the present invention may also include co-administration with other human factors. Exemplary cytokines or hematopoietins for such use include, without limitation, the known factors as IL-1, IL-2, IL-3, IL-4, IL-5, IL-6, IL-7, IL-9, IL-11, GM-CSF, G-CSF, CSF-1 or erythropoietin. Of particular interest are X-IL3 fusion where X is G-CSF, GM-CSF, IL11, IL7 or IL-9. Growth factors like B cell growth factor, B cell differentiation factor, or eosinophil differentiation factors may also prove useful in co-administration with the fusion protein IL3-X or X-IL3.

The following examples describe the construction and production of illustrative fusion proteins of this invention, IL3-IL3, IL3-GCSF, IL3-GMCSF and IL3-IL11, as well as other methods and products of the present invention. These examples are for illustration only and do not limit the scope of the present invention.

EXAMPLE 1

Construction of Multidomain IL-3 Molecules

To obtain an IL3-X fusion protein, two IL3 cDNA sequences [Genetics Institute, Cambridge, Mass.] were obtained according to the procedures described in PCT/US87/01702, which is incorporated herein by reference for its disclosure of the production of IL3 molecules. The two cDNA sequences were fused together with a short piece of DNA. This DNA encoded a linker peptide designed to allow the two IL3 proteins to fold and act independently of one another.

The sequence of this linker peptide was based on a sequence found in the HIV-1 reverse transcriptase as described above. The sequence of the linker used in this fusion is as follows:

| | Gly | Asp | Ala | Asn | Arg | Glu | Thr | Lys | Leu | Gly | Lys | Gly |
|---|---|---|---|---|---|---|---|---|---|---|---|---|
| C | GGT | GAT | GCT | AAC | CGT | GAA | ACT | AAG | CTT | GGT | AAA | GG |
| G | CCA | CTA | CGA | TTG | GCA | CTT | TGA | TTC | GAA | CCA | TTT | CCA T |

The scheme used to fuse the IL3 cDNAs and the linker region employs conventional recombinant engineering techniques as described in Maniatis et al, "Molecular Cloning, A Laboratory Manual", Cold Spring Harbor Laboratory, Cold Spring Harbor, N.Y. (1982). The construction of the fusions is outlined in FIG. I. Briefly described, the IL3 cDNA sequence, minus the sequence encoding its secretory leader, had the 5' and 3' ends that appear in the upper portion of Table A below. These IL3 sequences after digestion with NdeI and XbaI had the 5' and 3' ends that appear in the lower portion of Table A.

TABLE A

| 3' end of gene: | 5' end of gene: |
|---|---|
| ATC TTC TAG A | CAT ATG GCT |
| TAG AAG ATC T | GTA TAC CGA |
| Ile Phe stop | Met Ala |
| --XbaI- | --NdeI- |
| 3' end of gene: | 5' end of gene: |
| ATC TT | T ATG GCT |
| TAG AA | AC CGA |

The digested IL3 sequences were inserted into a plasmid pALhIL3-781 designed for expression of heterologous proteins intracellularly in *E. coli*. This plasmid is described for illustration only. The techniques described to produce the described fusion molecules may employ other plasmids containing the same or different component sequences, restriction sites and the like. This exemplary plasmid is a modified form of pAL181 [ATCC #40134] containing an additional transcriptional terminator sequence. Plasmid pALhIL3-781, as depicted in FIG. I, is characterized by the complete cDNA sequence of mature IL3 fused in frame with an initiator methionine and an appropriately spaced ribosome binding site; the major leftward promoter from phage lambda to control and drive transcription of the IL3 cDNA; a sequence beyond the 3'-end of the IL3 sequence which causes transcription to terminate; and three unique restriction sites within the plasmid. One site 5' to the IL3 gene and encompassing the coding sequence for the initiator methionine is NdeI. Another site is incorporated within the translation termination sequence in the 3' end of the IL3 gene, XbaI. The remaining site is 5' to the transcription termination sequence, HindIII.

Two samples of the plasmid were prepared. One was cut with NdeI and HindIII and the small fragment containing the IL3 cDNA was purified (see right side of FIG. I). The second was cut with XbaI, treated with Mung Bean exonuclease to remove the single-stranded DNA tails, and digested with HindIII. The larger fragment was isolated (see left side of FIG. I). The two isolated fragments were mixed with synthetic linker oligonucleotides of the sequence shown above and treated with T4-polynucleotide ligase.

The sequence of the junction region between the two IL3 sequences after ligation was as follows:

```
     Phe  Gly  Asp  Ala  Asn  Arg  Glu  Thr  Lys  Leu  Gly  Lys  Gly
TC   TTC  GGT  GAT  GCT  AAC  CGT  GAA  ACT  AAG  CTT  GGT  AAA  GGT
AG   AAG  CCA  CTA  CGA  TTG  GCA  CTT  TGA  TTC  GAA  CCA  TTT  CCA

Met
ATG  G
TAC  C
```

Plasmids in which the two IL-3 coding sequences and one or more linker sequences had been fused together were selected by colonies that hybridize to linker sequences and the sequence of the fusion junctions verified. The presence of plasmids with more than one linker inserted between the IL3 sequences was unexpected. These multiple linker plasmids probably arose from a small amount of nuclease contamination in the DNA ligase or some carry-over of Mung Bean nuclease which removed the TA single-stranded tail of the linker duplex allowing it to be ligated to the blunt end of an adjacent linker duplex.

Once the plasmids were constructed, they were transformed into appropriate *E. coli* strains, such as W3110 (lambda PamcI857) [M. Rosenberg et al, *Meth. Enzymol.*, 101:123–137 (1983) and Sambrook et al, cited above] for expression of the multidomain IL-3. The two plasmids selected for this experiment contained two IL-3 cDNA sequences separated by one and three linker sequences respectively. pALIL31-781 which contains one copy of the linker is illustrated in the lower portion of FIG. I. These fusion molecules produced proteins of 31 and 34 kilodaltons, respectively.

The proteins accumulated within the cells as insoluble inclusion bodies which were solubilized and refolded by standard methods [see, e.g., U.S. Pat. No. 4,512,922]. The resulting proteins, when tested in the CML assay described below in Example 7 demonstrated IL-3 activity equal to or greater than the activity of natural or recombinant IL-3.

EXAMPLE 2

IL3/GMCSF Fusion Proteins

An exemplary fusion protein of formula IL3-X was formed by fusing the IL3 cDNA sequence in frame with the DNA sequence encoding granulocyte-macrophage colony stimulating factor, GMCSF. The GMCSF cDNA sequence is described in published European patent application 188,479, which is incorporated by reference herein for disclosure of the sequence and methods for obtaining same. The two cDNA sequences were fused together with the short piece of linker DNA described in Example 1 by analogous techniques.

The scheme used to construct the DNA sequence which encodes the IL3-GMCSF fusion protein is provided schematically in FIG. II. The IL-3 cDNA was inserted into the expression plasmid, pAL181, modified as described in Example 1. The GMCSF cDNA, minus the sequence encoding its secretory leader, was inserted into an unmodified version of pAL181, resulting in plasmid pALC-186. The IL3 plasmid, pALhIL3781, was digested with XbaI and then treated with Mung Bean exonuclease to remove the single-stranded DNA tails. The plasmid was then digested with AvaI and the small resultant fragment carrying the IL3 coding sequence was isolated. The GMCSF expression plasmid, pALC-186, was digested with NdeI and AvaI, and the large fragment which carried the GMCSF gene was isolated. The two fragments were mixed with synthetic oligonucleotides encoding the linker peptide described in Example 1 and treated with T4-polynucleotide ligase. Plasmids were selected in which the IL3 cDNA, linker oligonucleotide, and the GMCSF cDNA sequences were fused contiguously to form a gene which encodes a protein with IL3 as its N-terminal domain and GMCSF as its C-terminal domain.

The plasmid carrying the gene for the IL3-GMCSF fusion protein, pALIL3-GM81, was transformed into an appropriate *E. coli* host strain as described in Example 1 for expression of the fusion protein.

EXAMPLE 3
IL3/GCSF Fusion Proteins

Another exemplary fusion protein of formula IL3-X was formed by fusing the IL3 cDNA sequence in frame with the DNA sequence encoding granulocyte-colony stimulating factor, GCSF. GCSF cDNA for this fusion was obtained from Genetics Institute, Inc. and had the sequence in PCT published application PCT/US86/01708; which is incorporated by reference herein for disclosure of the GCSF sequence and methods for obtaining same. This fusion molecule was constructed in a manner analogous to that described for IL3-IL3. Specifically, the fusion was mediated by the linker DNA sequence described in Example 1.

The scheme used to construct the DNA sequence which encodes an IL3-GCSF fusion protein is provided schematically in FIG. III. The IL3 and the GCSF cDNAs, minus these leader sequences, were inserted into the expression plasmids, pAL181, modified as described in Example 1. The IL3 expression plasmid pALhIL3781 was cut with XbaI, treated with Mung Bean exonuclease to remove the single-stranded DNA tails, and digested with HindIII. The larger fragment was isolated. The GCSF expression plasmid pALG$_a$781 was cut with NdeI and HindIII and the small fragment containing the GCSF gene was purified. The two isolated fragments were mixed with synthetic oligonucleotides encoding the same linker peptide used in Example 1 and treated with T4-polynucleotide ligase. Plasmids were selected in which the IL3 CDNA, linker oligonucleotide, and GCSF cDNA sequences were fused contiguously to form a gene which encodes a protein with IL3 as its N-terminal domain and GCSF as its C-terminal domain.

The plasmid carrying the gene for the IL3-GCSF fusion protein, pALIL3G781, was transformed into an appropriate *E. coli* host strain as described in Example 1 for expression of the fusion protein.

When expressed, the fusion protein accumulated within the cells as insoluble inclusion bodies which were solubilized and refolded by the standard methods described above. The resulting proteins had IL-3 activity and GCSF activity in the in vitro cell stimulation assays described in Example 7.

EXAMPLE 4
GCSF/IL3 Fusion Proteins

An exemplary fusion protein of formula X-IL3 was formed by fusing the IL-3 cDNA sequence in frame with, and 3' to, the DNA sequence encoding granulocyte-colony stimulating factor, GCSF. This fusion molecule was constructed in a manner analogous to that described for IL3/GCSF. Specifically, the fusion was mediated by the linker DNA sequence described in Example 1.

The scheme used to construct the DNA sequence which encodes the GCSF-IL3 fusion protein is provided schematically in FIG. III. The IL-3 and the GCSF cDNAs were inserted into the modified expression plasmids pAL181 described in Example 1. The GCSF cDNA had a StyI site at its 3' end and another one internal to the coding sequence of the gene. The internal site was changed by site-directed mutagenesis, leaving the protein sequence unaltered. The resultant plasmid, pALGIL3-781, was cut with StyI, treated with Mung Bean exonuclease to remove the single-strand DNA tails, and digested with HindIII. The larger fragment was isolated. The IL-3 expression plasmid, pALhIL3-781, was cut with NdeI and HindIII and the small fragment containing the IL-3 gene was purified. The two isolated fragments were mixed with synthetic oligonucleotides encoding the same linker peptide used in Example 1 and treated with T4-polynucleotide ligase. Plasmids were selected in which the GCSF, linker oligonucleotide, and IL-3 cDNA sequences were fused contiguously to form a gene which encodes a protein with GCSF as its N-terminal domain and IL-3 as its C-terminal domain.

The plasmid carrying the gene for the GCSF-IL3 fusion protein, pALGIL3-781, was transformed into an appropriate *E. coli* host strain as described in Example 1 for expression of the fusion protein.

When expressed, the fusion protein accumulated within the cells as insoluble inclusion bodies which were solubilized and refolded by the standard methods described above, e.g. described in U.S. Pat. No. 4,512,922. The resulting protein had both GSCF and IL-3 activity in the in vitro cell stimulation assays described in Example 7.

EXAMPLE 5
IL3/IL11 Fusion Protein

Another exemplary fusion protein of formula IL3-X was formed by fusing the IL3 cDNA sequence in frame with the DNA sequence encoding the mature form of interleukin IL11. The sequence of IL-11 and methods for obtaining it are described in detail in co-pending U.S. patent application Ser. No. 526,474, incorporated herein by reference. The IL11 cDNA was constructed from synthetic oligonucleotides to encode a protein which has the same primary amino acid sequence as found in human IL11, but using codons more compatible with bacterial expression than the native cDNA. The sequence of this modified IL11 gene is provided below in Table B. The gene fusion was constructed in a manner analogous to that described in Example 3. Specifically, the fusion was mediated by the linker DNA sequence described in Example 1.

TABLE B

| | | | | |
|---|---|---|---|---|
| ATGCCAGGTC | CACCACCAGG | TCCACCTCGA | GTTTCCCCAG | ACCCGCGCGC |
| TGAACTGGAC | AGCACAGTAC | TGCTGACCCG | CTCTCTGCTG | GCAGACACTC |
| GCCAGCTGGC | TGCACAGCTG | CGCGACAAAT | TCCCGGCTGA | CGGTGACCAC |
| AACCTGGATT | CCCTGCCGAC | CCTGGCTATG | AGCGCAGGTG | CACTGGGAGC |
| TCTGCAACTG | CCAGGTGTAC | TGACTCGCCT | GCGTGCAGAC | CTGCTGTCCT |

TABLE B-continued

| | | | | |
|---|---|---|---|---|
| ACCTGCGCCA | CGTTCAGTGG | CTGCGGCGCG | CAGGTGGCTC | TTCCCTGAAA |
| ACCCTGGAAC | CGGAGCTGGG | CACCCTGCAA | GCTCGCCTGG | ACCGCCTGCT |
| GCGCCGCCTG | CAGCTGCTGA | TGTCCCGCCT | GGCTCTGCCG | CAGCCACCAC |
| CGGACCCACC | AGCACCGCCG | CTGGCTCCAC | CATCCTCTGC | TTGGGGTGGT |
| ATCCGCGCAG | CTCACGCTAT | CCTGGGTGGT | CTGCACCTGA | CTCTGGACTG |
| GGCTGTTCGC | GGTCTGCTGC | TGCTGAAAAC | TCGCCTGTAA | TAG |

The scheme used to construct the DNA sequence which encodes an IL3-IL11 fusion protein is provided schematically in FIG. V. The IL3 expression plasmid, pALhIL3781, was treated as described in Example 3. The IL11 sequence was synthesized by ligating 70–90 bp oligonucleotides together in about 150 bp pieces and inserting them sequentially into expression plasmid, pAL181, to build up the entire gene. Once the entire IL11 coding sequence had been constructed, the plasmid, called pALIL1781, was capable of directing synthesis of the IL11 protein. The expression plasmid was digested with NdeI and HindIII and the small fragment containing the IL11 gene was purified. The two isolated fragments were mixed with synthetic oligonucleotides encoding the linker peptide described in Example 1 and treated with T4-polynucleotide ligase. Plasmids were selected in which the IL3 cDNA, linker oligonucleotide, and IL11 gene sequences were fused contiguously to form a new gene which encodes a protein with IL3 as its N-terminal domain and IL11 as its C-terminal domain.

The plasmid carrying the gene for the IL3-IL11 fusion protein, pALIL311-781, was transformed into an appropriate *E. coli* host strain as described in Example 1 for expression of the fusion protein. This fusion protein had activity in the T10 assay and IL-3 assays described in Example 7.

EXAMPLE 6
Expression of Recombinant IL3-X Fusion Proteins

To express the fusion proteins of the examples, the DNAs in the plasmids described above encoding the fusion proteins are transferred into appropriate expression vectors, of which numerous types are known in the art for mammalian, insect, yeast, fungal and bacterial expression, by standard molecular biology techniques.

a. Bacterial Expression Systems

One skilled in the art can manipulate the sequences encoding the IL3-X and X-IL3 proteins by eliminating any mammalian regulatory sequences flanking the coding sequences and inserting bacterial regulatory sequences to create bacterial vectors for intracellular or extracellular expression of the fusion proteins of the invention by bacterial cells. The DNA encoding the fusion proteins may be further modified to contain different codons to optimize bacterial expression as is known in the art. The sequences encoding the fusion proteins may be operatively linked in-frame to nucleotide sequences encoding a secretory leader polypeptide permitting bacterial expression, secretion and processing of the fusion proteins by methods known in the art. Alternatively the IL3-X or X-IL3 fusions may be constructed for intracellular expression and the protein isolated, mixed and refolded by procedures well known in the art. The fusion protein expressed through either route in bacterial host cells may then be recovered, purified, and/or characterized with respect to physicochemical, biochemical and/or clinical parameters, all by known methods.

b. Mammalian Cell Expression

To obtain expression of the fusion protein a vector for mammalian cells, pXM, and the general procedures described in Y. C. Yang et al, *Cell*, 47:3–10 (1986) may be used. See, also, Kaufman, *Proc. Natl. Acad. Sci. USA*, 82:689–693 (1985), Kaufman et al, *J. Mol. Biol.*, 159:511–521 (1982); and Kaufman, *Proc. Natl. Acad. Sci., USA*, 82:689–693 (1985) for descriptions of vector construction techniques and vector components useful in the practice of this invention.

One skilled in the art can also construct other mammalian expression vectors comparable to the pXM vector by, e.g., inserting the DNA sequences of the fusion proteins from the respective plasmids with appropriate enzymes and employing well-known recombinant genetic engineering techniques and other known vectors.

For stable integration of the vector DNAs, and for subsequent amplification of the integrated vector DNAs, both by conventional methods, CHO cells may be employed. The transformation of these vectors with IL3-X or X-IL3 into appropriate host cells can result in expression of the fusion proteins.

c. Insect or Yeast Cell Expression

Similar manipulations can be performed for the construction of an insect vector for expression of these fusion proteins in insect cells [See, e.g., procedures described in published European patent application 155,476].

Similarly yeast vectors are constructed employing yeast regulatory sequences to express the fusion protein in yeast cells to yield intracellularly expressed or secreted extracellular active fusion protein. [See, e.g., procedures described in published PCT application WO 86/00639 and European patent application EP 123,289.] Fungal vectors may also be employed in the expression of these fusion molecules.

In any of the expression systems described above, the resulting cell lines can be further,amplified by appropriate drug selection, resulting cell lines recloned and the level of expression assessed using the appropriate assay for the components of the IL3-X fusion protein.

EXAMPLE 7
Biological Activities of IL3-X

The following assays were performed using the fusion proteins described in the above examples.

a. CML Assay

The CML assay was performed essentially according to procedures described in *Blood*, 63(4):904–111 (1984). A stock of cells were obtained from a frozen bag of peripheral blood from a CML patient in stable phase. This bag was thawed and refrozen into 500 aliquots of $15 \times 10^6$ cells/vial. These cells, "CML 8-3", were used to test for the IL-3-like activity of the IL-3-X fusion polypeptides. One vial is thawed quickly at 37° C. the day before the assay is set up. The contents of the vial are then transferred to a 15 ml tube and washed 2 times with 5% Hi Human AB Serum in RPMI (GIBCO, RPMI1640) [HAB/RPMI]. The cells are incubated overnight in 5% HiHAb/RPMI at 5% $CO_2$ and 37° C. The following day the cells are removed from culture, ficolled, washed, recounted and set aside.

100 ul of 10% HIFCS2/RPMI medium containing the material to be assayed is plated in each well of a microtiter plate. The cells prepared above are spun down and resuspended at a concentration of 1.3 to $2 \times 10^5$ cells/ul in 10% HIFCS/RPMI. 100 uls of cells are plated in each well and incubated in the presence or absence of anti-human GMCSF antibodies at 37° C. in 5% $CO_2$ for 48 or 72 hours. Thereafter 0.5 uCi $^3$H-thymidine is added per well and the wells are incubated for 6 hours at 37° C. Cells are harvested using a filtration manifold device onto GFC Type C filter paper (Schleicher-Schuller), washed with phosphate buffered saline and dried. Filters are then immersed in scintillation fluid and counted for $^3$H uptake.

Based on the thymidine uptake measurement, the above described fusion proteins particularly the IL3-GCSF and IL3-IL3, are active in this assay in stimulating the proliferation of leukemic blast cells.

b. M07E Assay

The M07E cell line was derived from the peripheral blood of an infant with acute megakaryocytic leukemia. Growth of M07E cells is dependent on the presence in the medium of GM-CSF, IL3 or IL4.

M07E cells are grown in the presence of recombinant human IL-3 at an approximate concentration of 8 units per milliliter. The cells are used to test for the IL-3-like activity of the IL-3-X fusion polypeptides of Example 1. The assay is performed essentially as follows: Two to four days before the assay is set up, the cells are transferred to a 15 ml tube and washed 2 times with 5% Hi Human AB Serum in RPMI (GIBCO, RPMI 1640) [HAB/RPMI]. The cells are incubated overnight in 5% HiHAb/RPMI at 5% $CO_2$ and 37° C. The following day the cells are removed from culture, ficolled, washed two times, recounted and set aside.

100 ul of 10% HIFCS/DME+PS+glucose medium containing the material to be assayed is plated in each well of a microtiter plate. The cells prepared above are spun down and resuspended at a concentration of 1.3 to $2 \times 10^5$ cells/ul in 10% HIFCS/DME+PS+glucose. 50 cells per microliter are plated in each well and incubated in the presence or absence of anti-human GMCSF antibodies at 37° C. in 5% $CO_2$ for 72 hours. Thereafter 0.5 uCi $^3$H-thymidine is added per well and the wells are incubated for 4 hours at 37° C. Cells are harvested using a filtration manifold device onto GFC Type C filter paper (Schleicher-Schuller), washed with phosphate buffered saline and dried. Filters are then immersed in scintillation fluid and counted for $^3$H uptake.

Based on the thymidine uptake measurement, the IL3-containing fusion proteins are active in this assay in stimulating the proliferation of leukemic blast cells.

c. TF-1 Assay

The TF-1 cell line was derived from the bone marrow of a patient with erythroleukemia [T. Kitamura, University of Tokyo]. The cells are grown in the presence of recombinant human GM-CSF at a concentration of 100 units per milliliter. Three days prior to performing the assay the cells are fed. This assay is performed essentially as described above for the M07E and CML assays with the following changes:

25 cells/microliter in each well;

3 days incubation time;

4 hours pulse time;

counting time 1 minute two replicates.

Based on the thymidine uptake measurement, the fusion proteins are active in this assay in stimulating the proliferation of these bone marrow cells.

d. 32D Proliferation Assay 32D is a murine IL3-dependent cell line grown in RPMI with 10% heat inactivated fetal calf serum, 2 mM glutamine, and P/S with 20% WeHi 3B conditioned medium as a murine IL3 source. These cells grow in the presence of G-CSF.

This assay is a 24 hour proliferation assay in which a cell density of $10^5$ cells/ml in a 200 ul final volume is used. In U-bottomed microtitre wells, the final density is approximately $2 \times 10^4$ cells/well. Serial 5 fold dilutions are performed on standards and samples of 2the fusion polypeptides. The conditions for the thymidine uptake are a 4 hour pulse of tritiated thymidine (0.5 uCi/well) at the end of the assay. The cells are harvested and washed on an LKB cell harvester and counted on an LKB scintillation counter.

Strong G-CSF activity was detected in the assay with the IL3-GCSF and GCSF-IL3 fusion molecules compared to the G-CSF standard.

e. DA2 Proliferation Assay

DA2 is a murine IL3 dependent cell line with grows equally well in LIF. The cells are maintained in RPMI with 5% HIFCS, 2 mM glutamine, P/S and 10% H23pInd conditioned medium as a source of LIF. For this assay the same medium is employed as for the 32D assay. The cell density is $3.75 \times 10^4$ cells/ml in 200 ul final volume, or $7.5 \times 10^3$ cells/well in a U bottomed microtitre plate. As with the 32D assay, serial 5 fold dilutions are made of samples and standards. The thymidine uptake employs a 72 hour incubation with a 4 hour thymidine pule (0.5 uCi/well) at the end of the assay. Harvesting is the same as the previous assay.

The fusion molecules IL3-GCSF and GCSF-IL3 performed in a comparable fashion in this assay as they did for the 32D assay.

f. Modified T1165 Proliferation Assay

This assay was described in detail in copending United States patent application SN 07/526,474, incorporated by reference herein, to detect IL11 activity. Briefly, T1165 IL-6 dependent murine plasmacytoma cells [R. P. Nordan et al, *Science*, 233:566 (1986); and obtained from Dr. Nordan, National Institutes of Health] are routinely grown in RPMI supplemented with 10% heat-inactiyated fetal calf serum, 2 mM glutamine, 100 u/ml penicillin, 100 µg/ml streptomycin (all Gibco, Grand Island, N.Y.), $5 \times 10^{-5}$ M beta mercaptoethanol (Sigma Chemical Co., St. Louis, Mo.), and supplemented with 10–20 U/ml recombinant human IL-6 produced in CHO cells (Genetics Institute, Inc.). Two to four days following passage, the cells are removed from culture, washed to remove residual IL-6 and resuspended at a concentration of $7.5 \times 10^4$ to $1 \times 10^5$ cells/ml. Cells were selected from these T1165 cells which have proved to be most responsive to IL11. These responsive cells are called T10 cells for convenience.

Serial dilutions of the sample to be assayed (pALIL311-781-transfected *E. coli* conditioned medium) are made in duplicate in 100 μl of culture medium without IL-6 on 96-well microtiter plates. 100 μl of the T10 cell suspension is then added to each well and the plates are incubated at 37° C. for 2–3 days; 0.5 μCi of $^3$H-thymidine [DuPont, Wilmington, Del.] is added per well for the final six hours of the assay. Cells are harvested onto GFC type C filter paper (LKB), washed with water and ethanol and dried. The filters are then immersed in scintillation fluid and counted on an LKB flatbed scintillation counter. Proliferation is measured by $^3$H-thymidine uptake.

*E. coli* cell supernatants from transfection of the pALIL311-781 were assayed for activity. The IL3-IL11 fusion protein revealed IL-11 activity in this assay.

g. Murine Fibrin Clot Assay

The fusion molecule IL3-IL11 is tested for activity in the megakaryocyte colony formation assay performed substantially as described in S. Kuriya et al, *Exp. Hematol.*, 15:896–901 (1987). A fibrin clot is formed containing 2.5× $10^5$ mouse bone marrow cells in a 96-well plate. The diluted sample is layered around the clot and incubated for 6 days. Thereafter, cells are fixed and megakaryocytes stained for acetylcholinesterase, a specific marker for murine megakaryocytes. A colony is defined as three or more megakaryocytes per unit area. Two types of megakaryocyte colonies are routinely observed: pure megakaryocyte colonies containing no additional cell types, and mixed megakaryocyte colonies containing additional non-megakaryocyte cell types.

The following control samples are included in every assay. A positive control is WEHI conditioned medium (murine IL-3), which produces between 7–25 (average 12) megakaryocyte colonies per clot, approximately 50% pure and 50% mixed megakaryocyte colonies. Another positive control is serum taken from lethally irradiated dogs at the nadir of the platelet count [see Mazur et al, *Exp. Hematol.*, 13:1164–1172 (1985)], which produces between 6–22 (average 15) megakaryocyte colonies per clot, of which approximately 70% are pure and 30% are mixed megakaryocyte colonies. The negative control is Iscoves Medium, which produced 2–4 megakaryocyte colonies per clot.

In each assay the samples are tested in duplicate and in three dilutions. The assay results are expected to demonstrate that the IL3-IL11 fusion protein stimulates the production and maturation of megakaryocyte cells in this assay to a significant degree.

Numerous modifications and variations in practice of this invention are expected to occur to those skilled in the art.

I claim:

1. A protein having an amino acid sequence of the formula IL-3/X or X/IL-3 substantially free from association with other proteinaceous materials, wherein X is IL-3.

* * * * *